United States Patent
Bayat

(10) Patent No.: US 7,384,392 B2
(45) Date of Patent: Jun. 10, 2008

(54) DISPOSABLE EXPANDABLE CORDLESS LIGHTED RETRACTOR

(76) Inventor: Ardeshir Bayat, 11444 W. Olympic Blvd., 5th Floor, Los Angeles, CA (US) 90064

( * ) Notice: Subject to any disclaimer, the term of this patent is extended or adjusted under 35 U.S.C. 154(b) by 31 days.

(21) Appl. No.: 11/439,316

(22) Filed: May 22, 2006

(65) Prior Publication Data

US 2007/0270656 A1  Nov. 22, 2007

(51) Int. Cl.
*A61B 1/32* (2006.01)
(52) U.S. Cl. .................. 600/214; 600/245
(58) Field of Classification Search .......... 600/212, 600/214, 215, 219, 223, 224, 245, 210
See application file for complete search history.

(56) References Cited

U.S. PATENT DOCUMENTS

| | | | |
|---|---|---|---|
| 2,296,793 A | 9/1942 | Kirschbaum | |
| 3,638,644 A | * 2/1972 | Reick | 600/191 |
| 3,716,047 A | 2/1973 | Moore | |
| 4,052,980 A | 10/1977 | Grams et al. | |
| 4,337,763 A | 7/1982 | Petrassevich | |
| 4,562,832 A | 1/1986 | Wilder et al. | |
| 5,339,801 A | 8/1994 | Poloyko et al. | |
| 5,722,935 A | 3/1998 | Christian | |
| 5,967,971 A | 10/1999 | Bolser | |
| 6,080,105 A | 6/2000 | Spears | |
| 6,602,188 B2 | 8/2003 | Bolser | |
| 2003/0095781 A1 | 5/2003 | Williams | |

* cited by examiner

*Primary Examiner*—Cary E. O'Connor
(74) *Attorney, Agent, or Firm*—Cislo & Thomas, LLP

(57) ABSTRACT

A surgical instrument to manipulate a patient's tissues, comprising a handle, a first blade, a second blade, and a blade actuator, and may further comprise a light and a power source. The first blade and the second blade each extend from the handle. The second blade is divided into at least two segments. The segments are each pivotable in relation to each other along a common axis. Movement of the blade actuator causes the segments of the second blade to pivot radially toward and away from each other.

1 Claim, 5 Drawing Sheets

DISPOSABLE EXPANDABLE CORDLESS LIGHTED RETRACTOR

TECHNICAL FIELD

This invention relates to surgical instruments used to manipulate a patient's tissues, such as skin, bone, and muscle.

BACKGROUND ART

Surgical retractors and expanders are used to manipulate a patient's tissues, such as skin, muscle, or bone, and are commonly utilized by surgeons and dentists on the human body and by veterinarians on animals. Retractors have blades that tend to pull the tissue to create more room for a surgeon to view an area of interest, such as a body cavity, and to manipulate other surgical tools. Expanders perform a similar function by tending to push the tissue instead of pulling it. Retractors and expanders are available in a variety of blade sizes and shapes to pull and push different body tissues in different locations on the body. For example, the blade can be curved to lift or separate a portion of the patient's tissues. When both retraction and expansion are needed, a surgeon commonly uses a separate device for each function. This further crowds the patient's body cavity and often requires additional operating assistants to manipulate and hold each device.

While manipulating the patient's tissues, it is important to adequately illuminate the corresponding region of the patient's body. As ambient light is not always sufficient to light a body cavity, illumination is commonly accomplished by a separate light. This light generally must then be held in place near the body cavity by an operating assistant or by some sort of rigging, further crowding the surgical area.

Furthermore, many of the existing devices must be sterilized between uses, a process that may be expensive and time-consuming. Even with sterilization procedures, however, there remains a risk of pathogen cross infection because the instrument will be used more than once. Furthermore, such instruments are often made of metal and are difficult to hold for long periods of time.

There is therefore a need for a surgical instrument that combines the functions of retraction, expansion, and illumination into a single device while remaining easy to handle. There is further a need for such an instrument to be disposable after a single use, yet remain economical.

DISCLOSURE OF INVENTION

The present invention is directed to a surgical instrument to manipulate a patient's tissues. The surgical instrument has a handle, a first blade, a second blade, and a blade actuator. The instrument may further have a light, a power source, and a light switch. The handle, the first blade, and the second blade may each be made of a plastic polymer that is sturdy yet disposable.

The first blade and the second blade extend from the base end of the handle. The second blade is divided into at least two segments, where each segment is pivotable in relation to the other about a common axis. Movement of the blade actuator to a first position causes the segments of the second blade to pivot about the common axis.

BEST MODE FOR CARRYING OUT THE INVENTION

Figure 1:
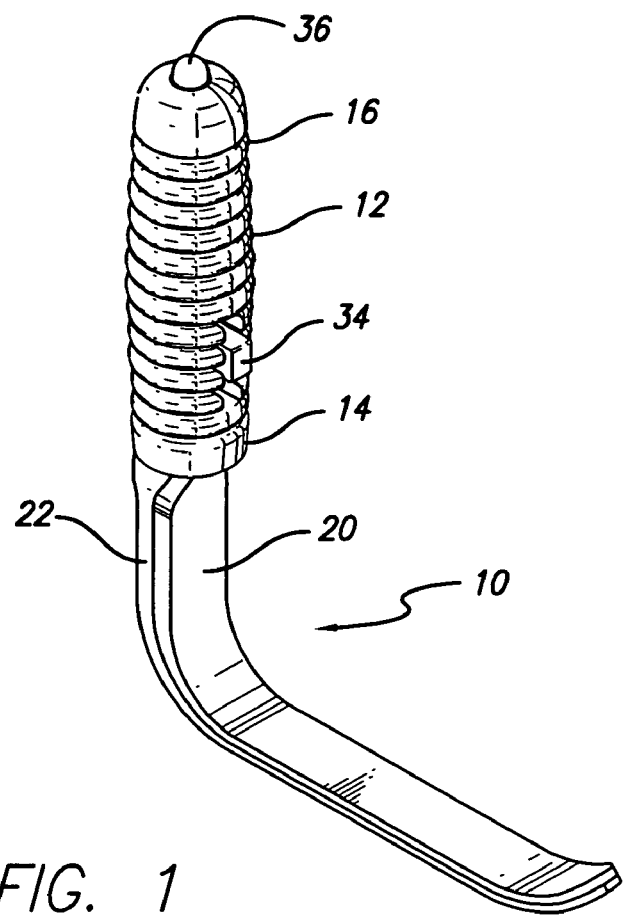
FIG. 1 is a perspective view of an embodiment of a surgical instrument in accordance with the present invention, showing a retracted position.

The detailed description set forth below in connection with the appended drawings is intended as a description of presently preferred embodiments of the invention and is not intended to represent the only forms in which the present invention may be constructed or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Referring to the accompanying figures, a surgical instrument 10 allows a user to manipulate and illuminate a patient's tissues 32. The manipulation, for example, may be expansion or retraction of the patient's skin, muscle, or bone. Expansion and retraction may also be performed simultaneously. The surgical instrument 10 comprises a handle member 12, a first blade 20, a second blade 22, and a blade actuator 34. The surgical instrument 10 may further comprise a light 30, a power source 38, and a light switch 36.

The handle member 12 may be configured to be hand-held and may comprise a grip handle, cylindrical grip, or other ergonomic design to be held by a user. In some embodiments, the handle member 12 may have protrusions such as vertical or horizontal ridges, to facilitate comfortable holding by the user. In some embodiments, the handle member 12 may have a flared top to allow the handle member to be more easily gripped and held. It is further contemplated that the handle member 12 may have a soft, foam plastic material to provide a comfortable, resilient grip. In some embodiments, the handle member 12 may be shaped to permit connection to a holding device or other device for mounting the surgical instrument to a surgical table or to a floor stand. It is also contemplated that the handle member 12 may have a channel or tube extending through it to the first blade 20. The channel or tube may be connected to a suction device, such as a suction tap in an operating room, to provide aspiration of gas or fluid from the region of the patient's tissues adjacent to the surgical instrument 10.

In some embodiments, the surgical instrument 10 may be composed of materials permitting it to be readily and economically disposable. For example, the handle member 12, the first blade 20, and the second blade 22 may each be made of a plastic polymer. The plastic polymer is preferably a lightweight, medical grade polymer and most preferably is a polycarbonate.

The first blade, or tang, 20 extends from the base end 14 of the handle member 12 and may be generally flat and generally rectangular in profile, such as shown in FIG. 1. However, it is equally contemplated that other blade profiles or cross-sections sufficient to manipulate the patient's tissues may be used, such as cylindrical, paddle-shaped, rectangular, or conical. In some embodiments, at least a portion of the length of the first blade 20 may be generally oblique to the handle member 12. In the depicted embodiments, the first blade 20 is generally perpendicular to the handle member 12. It is equally contemplated that the first blade 20 could be at any angle to the handle member 12, and it is contemplated that the angle may be adjustable, such as by inclusion of a hinge in the blade or at the attachment point of the blade with the handle member 12.

In some embodiments, the first blade 20 may be ribbed or ridged to add structural integrity and increased strength to the blade. In some embodiments, the first blade 20 may have a flared tip, where the tip is oblique to the adjacent portion of the blade, such as what is shown in FIG. 1. Such flared tips facilitate movement of the tip among the patient's tissues. In some embodiments, the first blade 20 may have tines, or teeth, at the tip to grip or maneuver the tissues. It is further contemplated that, in some embodiments, the first blade 20 may be extendable or adjustable. In such embodiments, the length or width of the blade may be made longer or shorter, for example, by sliding one portion of the blade relative to another portion.

The second blade, or tang, 22 also extends from the base end 14 of the handle member 12, may be generally flat, generally rectangular in profile, and may have at least a portion of its length generally oblique to the handle. It is equally contemplated that the second blade 22 could be at any angle to the handle member 12, and it is contemplated that the angle may be adjustable, such as by inclusion of a hinge at a bend in the blade or at the attachment point of the blade with the handle member 12. As with the first blade 20, additional blade profiles and cross-sections are equally contemplated by the invention, and the second blade 22 may be ribbed or ridged to add structural integrity and increased strength to the blade. In some embodiments, the second blade 22 may have a flared tip, like what is shown in FIG. 1. In some embodiments, the second blade 22 may have tines, or teeth, instead of a rounded tip. In some embodiments, the first blade 20 may have tines, or teeth, at the tip to grip or maneuver the tissues. It is further contemplated that, in some embodiments, the second blade 22 may be extendable or adjustable. In such embodiments, the length or width of the blade may be made longer or shorter, for example, by sliding one portion of the blade relative to another portion.

The second blade 22 is divided, for example longitudinally, into a left segment 24 and a right segment 26. The left segment 24 and right segment 26 are in pivotal relation to each other. In some embodiments, the left segment 24 and right segment 26 are each rotatable about the base end 14 of the handle member 12, where the axis of pivoting 28 is generally along, or collinear to, the centerline 18 of the handle member 12.

Figure 2:
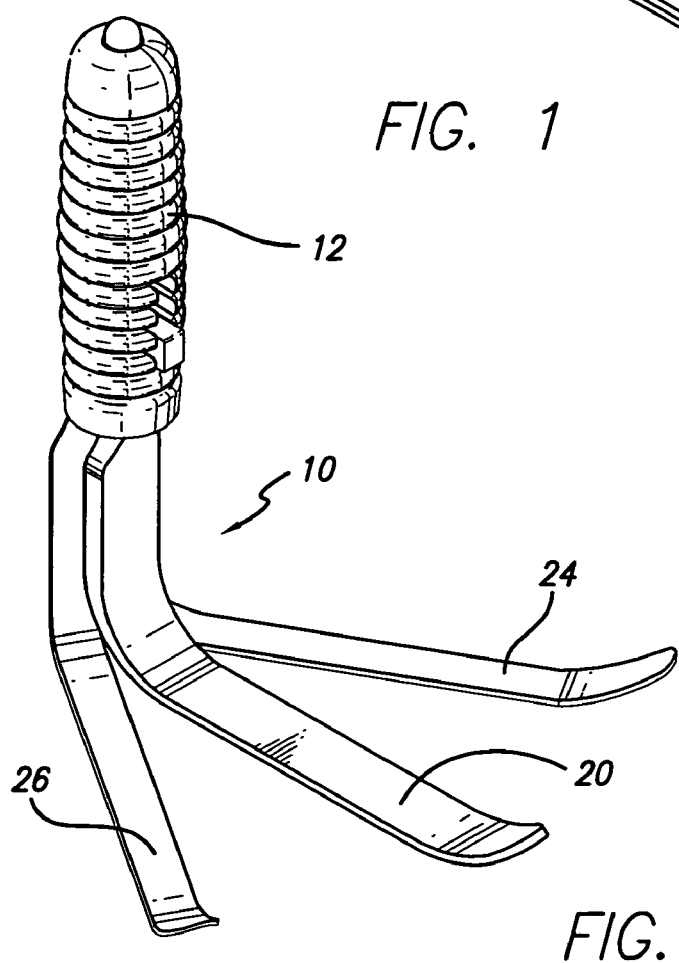
FIG. 2 is a perspective view of an embodiment of a surgical instrument, showing an extended position.
Figure 3:
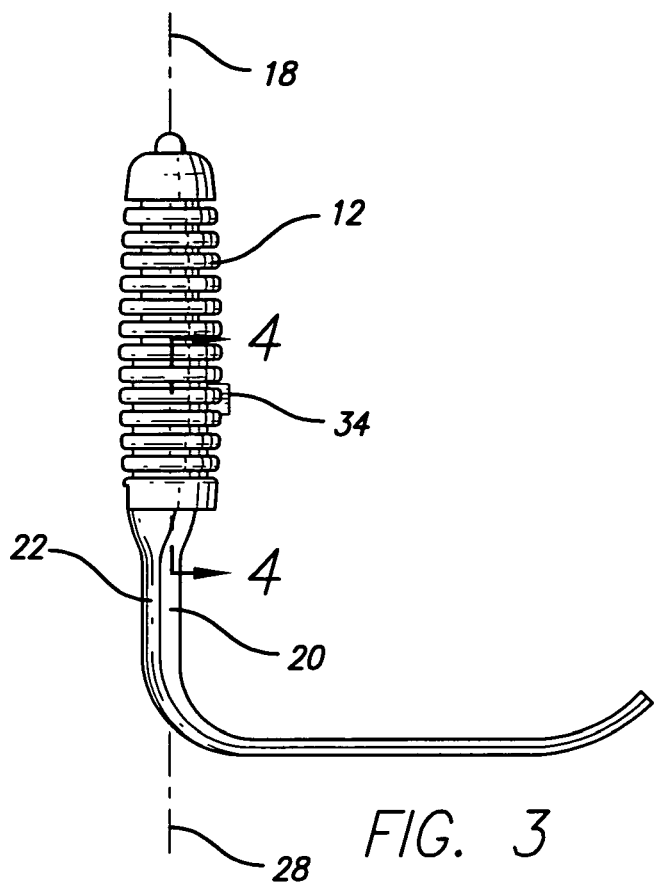
FIG. 3 is a side view of an embodiment of a surgical instrument.

In the embodiment shown in FIG. 2, the second blade 22 is positioned just below the first blade 20. The present invention, however, contemplates other such configurations, such as positioning the second blade 22 just above the first blade 20 or positioning the left segment 24 and right segment 26 on either side of the first blade 20. It is further contemplated that embodiments of the invention may have more than two blades, and it is contemplated that the blades may not be on the same side of the handle. For example, a blade might be at an angle, such as 90° or 180°, to another blade.

The blade actuator 34 positions the left segment 24 and right segment 26 of the second blade 22. Movement of the blade actuator 34 to a first position causes the segments of the second blade 22 to pivot such that the left segment 24 and the right segment 26 are separated, defining an extended position of the second blade. Such an extended position is depicted in FIG. 2. Movement of the blade actuator 34 to a second position causes the segments of the second blade 22 to pivot such that the left segment 24 and the right segment 26 come together, defining a retracted position of the second blade. Such a retracted position is depicted in FIG. 1. Furthermore, in some embodiments a plurality of positions between the retracted position and the extended position are achievable by positioning the blade actuator 34 in a plurality of positions intermediate the first position and the second position. In the depicted embodiment, the second blade 22 is generally parallel to the first blade 20 when the second blade 22 is in the retracted position.

The blade actuator 34 may be located on the handle member 12 and may comprise a sliding switch. In an embodiment of the invention, the blade retractor 34 may be locked into the first position, the second position, or the plurality of intermediate positions. The locking mechanism may be in the form of one or more detents to engage and hold the blade retractor 34 in the selected position. For example, the detents may be recesses into which the blade retractor 34 can be moved and held in place by. The blade retractor 34, in some embodiments, may position the left segment 24 and right segment 26 of the second blade 22 by translating the motion of the blade retractor 34 to the segments by way of a cam and follower, gear arrangement, four-bar mechanism, lever, electric motor, hydraulic or pneumatic actuator, or other method known in the art.

Figure 7:
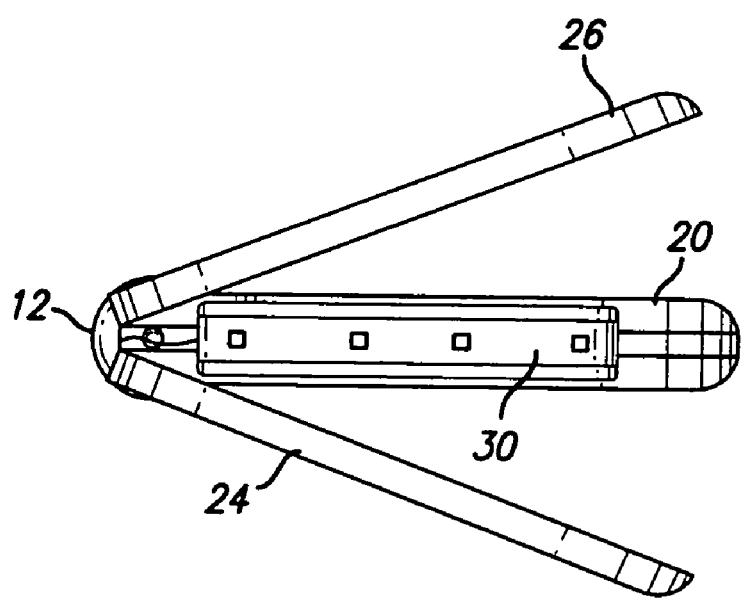
FIG. 7 is a bottom view of an embodiment of a surgical instrument, showing an extended position and having an array of LED's.

The light 30 may comprise at least one light emitting diode. Furthermore, the light 30 may be at the base end 14 of the handle member 12. The light 30 illuminates the patient's tissues immediately adjacent to or proximate the blades. In an embodiment, the light 30 may be on located on at least one of the first blade 20 and the second blade 22. Preferably, the light 30 is located on the underside of the first blade 20 and comprises one or more light emitting diodes. Refer to FIG. 7. It is further contemplated that the light 30 may be located within the profile of the blade. In such embodiments, the portion of the blade near the light 30 is constructed of a translucent or transparent material to allow the light to pass through the blade to illuminate the patient's tissues.

Figure 4:
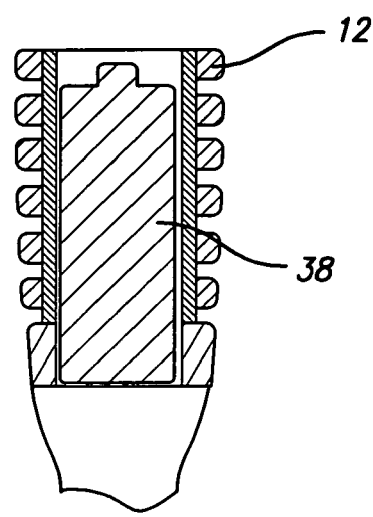
FIG. 4 is a partial cutaway of an embodiment of a surgical instrument.
Figure 5:
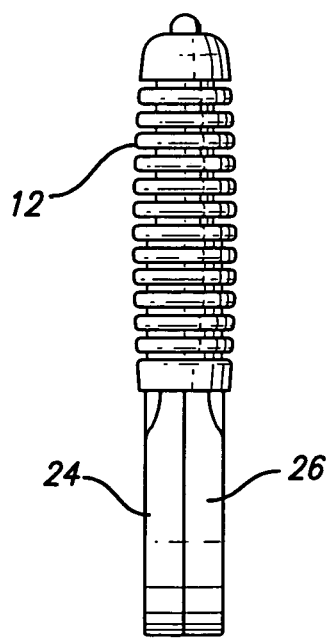
FIG. 5 is a rear view of an embodiment of a surgical instrument.
Figure 6:
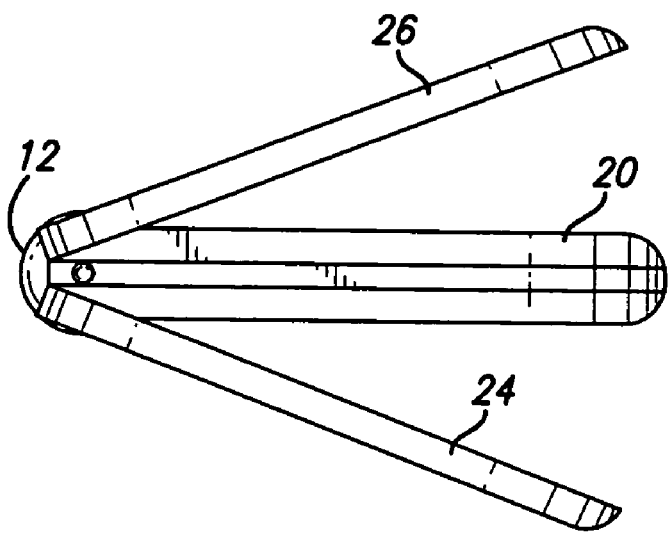
FIG. 6 is a bottom view of an embodiment of a surgical instrument, showing an extended position.

The power source 38 may be located within the handle member 12 and may comprise at least one battery, preferably two AAA-sized batteries. See, for example, FIG. 4. Such batteries allow the surgical device 10 to function for up to five hours. As the typical breast augmentation surgery lasts about one hour and other typical surgeries last three to four hours, a five hour battery life is normally sufficient. In addition, there may be a light switch 36 to interrupt and reestablish the electrical communication between the power source 38 and the light 30. The light switch 36 is preferably a button-type, toggle switch located at the top end 16 of the handle member 12. It is also contemplated that the light switch 36 be a dial or sliding switch. The light switch 36 may be used to select a low level, a high level of emitted light, or a plurality of levels between the low level and the high level.

Figure 8:
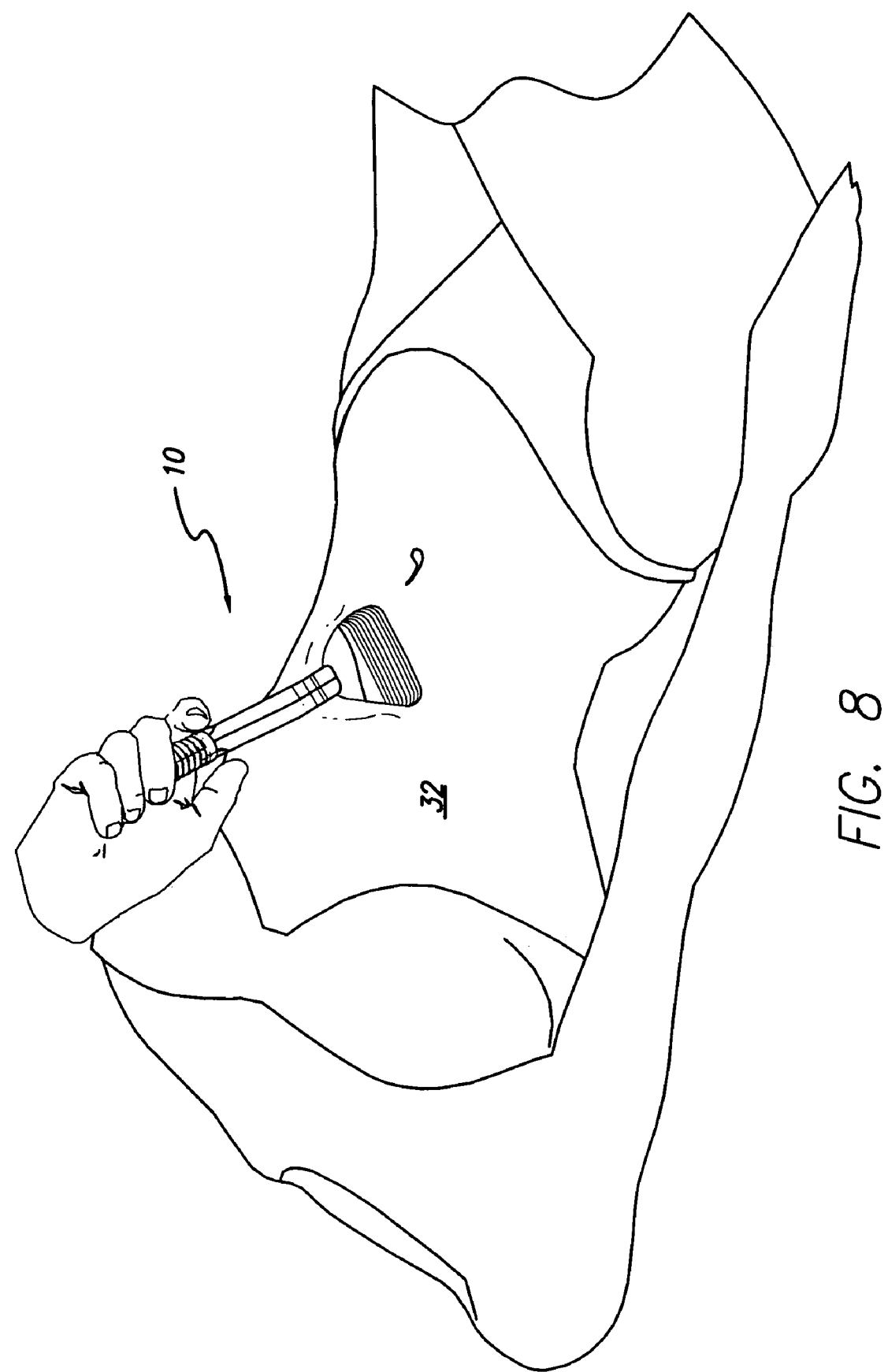
FIG. 8 is a depiction of how a surgical instrument in accordance with the present invention might be used.
Figure 9:
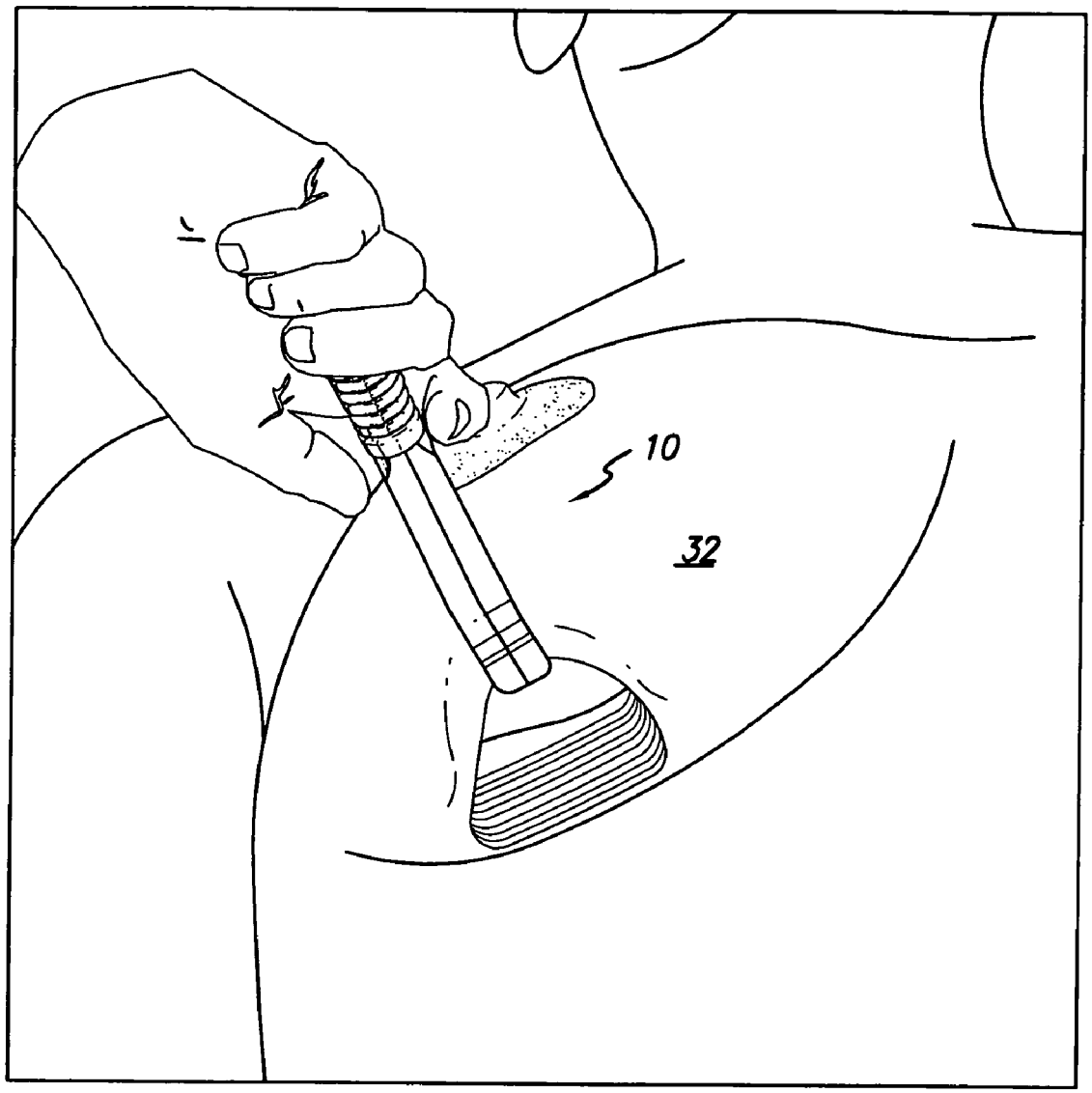
FIG. 9 is a depiction of how a surgical instrument in accordance with the present invention might be used.

While the present invention has been described with regards to particular embodiments, it is recognized that additional variations of the present invention may be devised without departing from the inventive concept. For example, while the depicted embodiments are suitable for manipulation of the tissues of a human being, particularly during plastic surgeries such as breast augmentation (see, for example FIGS. 8-9), it is equally contemplated that the surgical instrument may be used for other surgical procedures and on other regions of the patient's body. It is furthermore contemplated that the surgical instrument may be used by persons such as veterinary surgeons to manipulate the tissues of animals.

INDUSTRIAL APPLICABILITY

This invention may be industrially applied to surgical instruments used to manipulate a patient's tissues, such as skin, bone, and muscle.

What is claimed is:

1. A hand-held, disposable, surgical instrument to manipulate a patient's tissues, comprising:
    (a) a grip handle, shaped and dimensioned to be held by a user's hand and having a base end, a top end, and a centerline, the grip handle comprising a polycarbonate;
    (b) a first blade extending from the base end of the grip handle and having an underside, the blade being generally flat and having at least a portion of its length generally perpendicular to the grip handle, the first blade comprising a polycarbonate;
    (c) a second blade extending from the base end of the grip handle, the blade being generally flat and having at least a portion of its length generally perpendicular to the grip handle, the second blade being divided longitudinally into a left segment and a right segment, the left segment and the right segment each being pivotable about the base end of the grip handle, the axis of pivoting being generally collinear with the centerline of the grip handle, the second blade comprising a polycarbonate;
    (d) a blade actuator on the grip handle, comprising a sliding switch, whereby movement of the sliding switch to a first position causes the segments of the second blade to pivot about the base end of the grip handle such that the left segment and the right segment are separated, thereby defining an expanded position of the second blade, whereby movement of the sliding switch to a second position causes the segments of the second blade to pivot about the base end of the grip handle such that the left segment and the right segment come together, thereby defining a retracted position of the second blade, the second blade being generally parallel to the first blade when the second blade is in the retracted position;
    (e) a light at the underside of the first blade, the light comprising at least one light emitting diode positioned to illuminate the patient's tissues proximate the first blade and the second blade;
    (f) a power source within the grip handle and in electrical communication with the light, the power source comprising at least one battery; and
    (g) a light switch at the top end of the grip handle to interrupt and reestablish the electrical communication between the power supply and the light, the light switch comprising a push-button toggle.

* * * * *